(12) United States Patent
Tsuruta

(10) Patent No.: US 12,193,877 B2
(45) Date of Patent: Jan. 14, 2025

(54) ULTRASOUND ENDOSCOPE AND ENDOSCOPE SYSTEM

(71) Applicant: OLYMPUS CORPORATION, Tokyo (JP)

(72) Inventor: Teppei Tsuruta, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 615 days.

(21) Appl. No.: 17/376,698

(22) Filed: Jul. 15, 2021

(65) Prior Publication Data

US 2021/0338066 A1 Nov. 4, 2021

Related U.S. Application Data

(63) Continuation of application No. PCT/JP2019/001929, filed on Jan. 22, 2019.

(51) Int. Cl.
*A61B 8/00* (2006.01)
*A61B 1/00* (2006.01)
(Continued)

(52) U.S. Cl.
CPC ........ *A61B 8/4461* (2013.01); *A61B 1/00045* (2013.01); *A61B 1/00082* (2013.01);
(Continued)

(58) Field of Classification Search
CPC ............ A61B 1/00082; A61B 1/00087; A61B 1/00045; A61B 1/00098; A61B 1/00154;
(Continued)

(56) References Cited

U.S. PATENT DOCUMENTS 5,060,632 A * 10/1991 Hibino ............... A61B 1/00042
600/109
5,471,988 A * 12/1995 Fujio ..................... A61B 8/445
601/3
(Continued)

FOREIGN PATENT DOCUMENTS

DE 102005040528 A1 * 3/2006 ......... A61B 1/00006
JP 07-008496 A 1/1995
(Continued)

OTHER PUBLICATIONS

International Search Report dated Apr. 16, 2019 received in PCT/JP2019/001929.

*Primary Examiner* — Ryan N Henderson
*Assistant Examiner* — Timothy Tuan Luu
(74) *Attorney, Agent, or Firm* — Scully, Scott, Murphy & Presser, P.C.

(57) ABSTRACT

An ultrasound endoscope includes: a first rigid portion that is positioned at a front end of an insertion portion to be inserted inside a subject; a supporting portion that is connected to a proximal end of the first rigid portion and that has a long side along a longitudinal direction of the insertion portion; a second rigid portion that is connected to a proximal end of the supporting portion; an ultrasound transducer that is fixed to the supporting portion and that includes a plurality of piezoelectric elements arranged therein along the longitudinal direction of the insertion portion; a rotation mechanism configured to rotate the supporting portion and the ultrasound transducer in an integrated manner; and an angle display portion configured to indicate a state of the insertion portion corresponding to a rotation amount of the ultrasound transducer.

19 Claims, 8 Drawing Sheets

(51) Int. Cl.
*A61B 1/005* (2006.01)
*A61B 1/018* (2006.01)
*A61B 8/08* (2006.01)
*A61B 8/12* (2006.01)
*A61B 90/00* (2016.01)

(52) U.S. Cl.
CPC .......... *A61B 1/00087* (2013.01); *A61B 1/005* (2013.01); *A61B 1/018* (2013.01); *A61B 8/12* (2013.01); *A61B 8/4494* (2013.01); *A61B 8/466* (2013.01); *A61B 8/483* (2013.01); *A61B 90/06* (2016.02); *A61B 2090/067* (2016.02)

(58) Field of Classification Search
CPC ....... A61B 1/01; A61B 8/4461; A61B 8/4494; A61B 90/06; A61B 2090/067; A61B 1/0005; A61B 8/4466; A61B 8/445; A61B 8/4444; A61B 8/4245; A61B 8/12–15; A61B 1/0124; A61B 1/0126; A61B 1/0128

See application file for complete search history.

(56) References Cited

U.S. PATENT DOCUMENTS

| | | | | |
|---|---|---|---|---|
| 5,485,845 | A * | 1/1996 | Verdonk | G01S 15/874 600/463 |
| 6,461,314 | B1 * | 10/2002 | Pant | A61B 8/445 601/2 |
| 2008/0312536 | A1 * | 12/2008 | Dala-Krishna | A61B 8/12 600/459 |
| 2009/0177093 | A1 * | 7/2009 | Zelenka | A61B 1/126 600/463 |
| 2014/0309655 | A1 * | 10/2014 | Gal | A61B 90/37 606/127 |
| 2016/0331476 | A1 * | 11/2016 | Yoon | A61B 17/00234 |
| 2019/0208641 | A1 * | 7/2019 | Yates | G16H 20/40 |

FOREIGN PATENT DOCUMENTS

| | | | | |
|---|---|---|---|---|
| JP | 07-227395 A | | 8/1995 | |
| JP | 2004-209125 A | | 7/2004 | |
| JP | 2010000210 A | * | 1/2010 | |
| WO | WO-2016207692 A1 | * | 12/2016 | A61B 1/05 |

* cited by examiner

ULTRASOUND ENDOSCOPE AND ENDOSCOPE SYSTEM

CROSS-REFERENCE TO RELATED APPLICATION

This application is a continuation of International Application No. PCT/JP2019/001929, filed on Jan. 22, 2019, the entire contents of which are incorporated herein by reference.

BACKGROUND

1. Technical Field

The present disclosure is related to an ultrasound endoscope and an endoscope system.

2. Related Art

In the related art, an ultrasound endoscope is known that has a flexible and elongated insertion portion meant to be inserted inside a subject, and that observes the inside of the subject by sending and receiving ultrasound waves using an ultrasound transducer installed at the front end of the insertion portion (for example, refer to Japanese Patent Application Laid-open No. 2004-209125). Moreover, an endoscope system is known that includes an ultrasound endoscope, and includes an ultrasound imaging apparatus that receives electrical echo signals, which are obtained as a result of conversion of the ultrasound waves sent and received by the ultrasound endoscope, and generates ultrasound images.

SUMMARY

In some embodiments, an ultrasound endoscope includes: a first rigid portion that is positioned at a front end of an insertion portion to be inserted inside a subject; a supporting portion that is connected to a proximal end of the first rigid portion and that has a long side along a longitudinal direction of the insertion portion; a second rigid portion that is connected to a proximal end of the supporting portion; an ultrasound transducer that is fixed to the supporting portion and that includes a plurality of piezoelectric elements arranged therein along the longitudinal direction of the insertion portion; a rotation mechanism configured to rotate the supporting portion and the ultrasound transducer in an integrated manner; and an angle display portion configured to indicate a state of the insertion portion corresponding to a rotation amount of the ultrasound transducer.

In some embodiments, an endoscope system includes: an ultrasound endoscope; and an ultrasound imaging apparatus. The ultrasound endoscope includes a first rigid portion that is positioned at a front end of an insertion portion to be inserted inside a subject, a supporting portion that is connected to a proximal end of the first rigid portion and that has a long side along a longitudinal direction of the insertion portion, a second rigid portion that is connected to a proximal end of the supporting portion, an ultrasound transducer that is fixed to the supporting portion and that includes a plurality of piezoelectric elements arranged therein along the longitudinal direction of the insertion portion, and a rotation mechanism configured to rotate the supporting portion and the ultrasound transducer in an integrated manner. The ultrasound imaging apparatus is configured to send electrical pulse signals to the ultrasound endoscope, radiate ultrasound waves, receive an electrical echo signal obtained as a result of conversion of an ultrasound echo received by the ultrasound endoscope, generate an ultrasound image, and cause a display to display a state of the insertion portion corresponding to a rotation amount of the ultrasound transducer.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
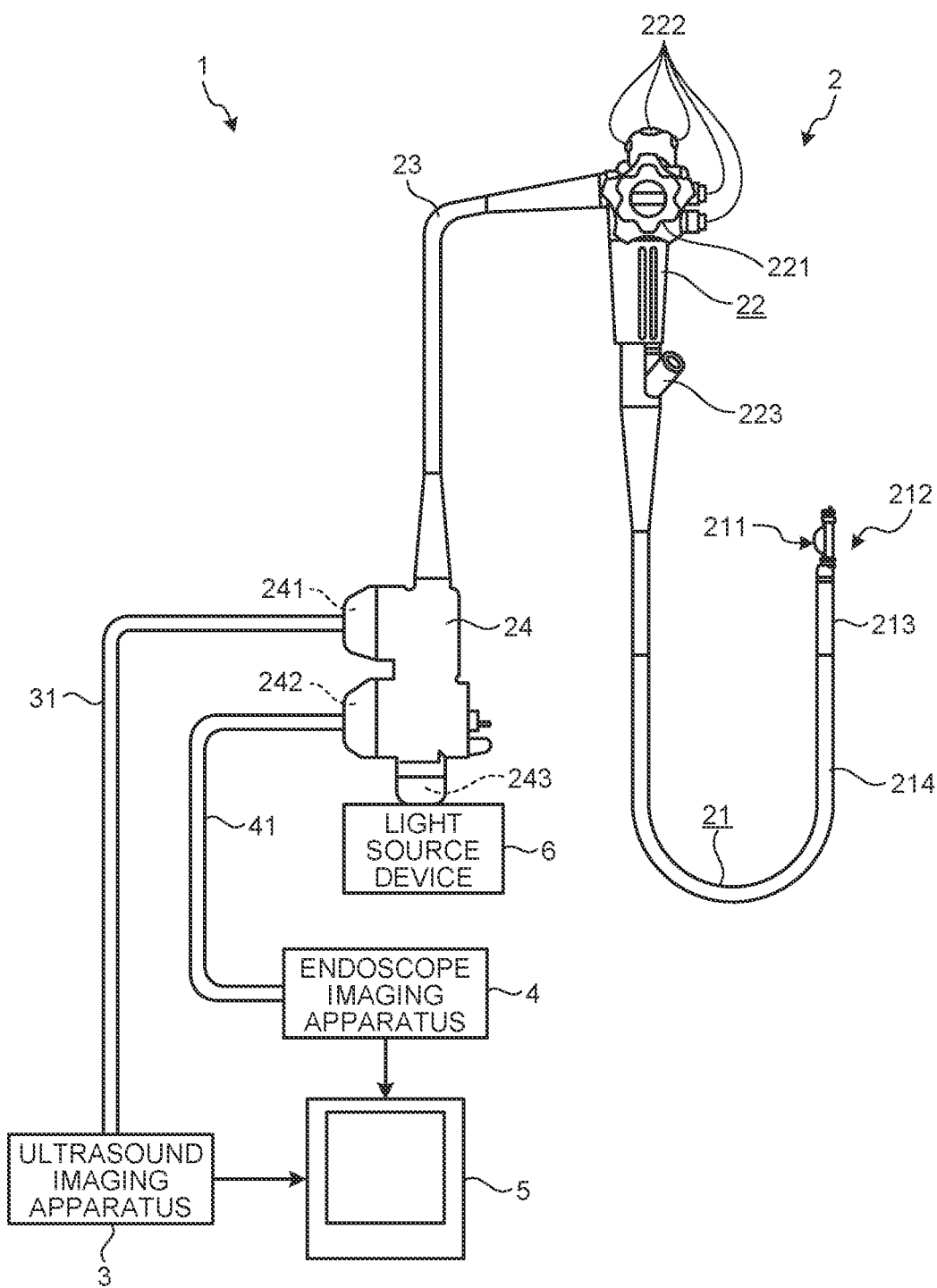
FIG. 1 is a diagram that schematically illustrates an endoscope system including an ultrasound endoscope according to an embodiment of the disclosure.

An exemplary embodiment of an ultrasound endoscope and an endoscope system according to the disclosure is described below with reference to the accompanying drawings. However, the disclosure is not limited by the embodiment described below. Moreover, the disclosure can be applied in general to an ultrasound endoscope including an ultrasound transducer, and to an endoscope system.

Meanwhile, in the drawings, identical or corresponding elements are referred to by the same reference numerals. Moreover, each drawing is schematic in nature, and it needs to be kept in mind that the relationships among the dimensions of the elements or the ratio of the elements may be different than the actual situation. Among the drawings too, there may be portions having different relationships among the dimensions or having different ratios among the dimensions.

Embodiment

FIG. 1 is a diagram that schematically illustrates the endoscope system including the ultrasound endoscope according to the embodiment of the disclosure. As illustrated in FIG. 1, an endoscope system 1 includes an ultrasound endoscope 2, an ultrasound imaging apparatus 3, an endoscope imaging apparatus 4, a display device 5, and a light source device 6.

The ultrasound endoscope 2 converts electrical pulse signals, which are received from the ultrasound imaging apparatus 3, into ultrasound pulses (acoustic pulses) using an ultrasound transducer installed at its front end, and irradiates the subject with the ultrasound pulses; and then converts the ultrasound echo reflected from the subject into electrical echo signals expressed in terms of voltage variation, and outputs the electrical echo signals.

The ultrasound endoscope 2 includes an imaging optical system and an imaging element. The ultrasound endoscope 2 is inserted into the alimentary tract (the esophagus, the stomach, the duodenum, or the large intestine) or into a respiratory organ (the trachea or the bronchus), and is capable of capturing images of the alimentary canal or the respiratory organ. Moreover, the ultrasound endoscope 2 includes a light guide for guiding an illumination light that is thrown onto the subject at the time of imaging. The light guide has the front end thereof reaching the front end of the insertion portion of the ultrasound endoscope 2 that is to be inserted into the subject, and has the proximal end thereof connected to the light source device 6 that generates the illumination light. Furthermore, the ultrasound endoscope 2 sends ultrasound waves to the surrounding organs of the alimentary tract or the respiratory organ (such as to the pancreas, the gallbladder, the biliary duct, the biliary tract, the lymph node, the mediastinal organs, and the blood vessels), and receives the ultrasound waves reflected from those surrounding organs.

As illustrated in FIG. 1, the ultrasound endoscope 2 includes an insertion portion 21, an operating unit 22, a universal cord 23, and a connector 24. The insertion portion 21 gets inserted into the subject. As illustrated in FIG. 1, the insertion portion 21 is positioned at the front end, and has a front end portion 212 holding an ultrasound transducer 211; has a curved portion 213 that is connected to the proximal end of the front end portion 212 and is bendable in nature; and a flexible tube 214 that is connected to the proximal end of the curved portion 213 and that has flexibility.

The ultrasound transducer 211 includes a plurality of piezoelectric elements arranged along the long side of the insertion portion 21. More particularly, the ultrasound transducer 211 is a convex transducer in which a longitudinal direction of the plurality of piezoelectric elements is orthogonal to the longitudinal direction of the insertion portion 21, and the piezoelectric elements are arranged to form a curved surface. Moreover, to the piezoelectric elements, a flexible shaft 211a (see FIG. 5) (explained later) and a plurality of signal lines 211b (see FIG. 5) (explained later) are connected. Moreover, to the piezoelectric elements, an acoustic matching layer (not illustrated) is attached as may be necessary, an acoustic lens 211c (see FIG. 4) is attached, and a backing member (not illustrated) is attached. The ultrasound waves generated in each piezoelectric element are irradiated toward the subject through the acoustic lens 211c. The configuration including a plurality of piezoelectric elements is housed in a housing 211d (see FIG. 2). Meanwhile, alternatively, the ultrasound transducer 211 can be a linear transducer in which a plurality of piezoelectric elements is arranged in a plane. Meanwhile, when the ultrasound transducer 211 is a convex transducer, the ultrasound waves are irradiated in a radial manner from a plurality of piezoelectric elements, and hence a wide observable range is achieved. On the other hand, when the ultrasound transducer 211 is a linear transducer, the front end of the insertion portion 21 can be made thinner as compared to a convex transducer. The ultrasound endoscope 2 performs electronic scanning by electronically switching among the piezoelectric elements involved in transmission and reception and by applying delays in the transmission and reception performed by the piezoelectric elements. Regarding the front end of the insertion portion 21, the detailed explanation is given later.

The operating unit 22 is connected to the proximal end of the insertion portion 21, and receives various operations from the operator such as a doctor. As illustrated in FIG. 1, the operating unit 22 includes a curved knob 221 that is meant for bending the curved portion 213, and includes a plurality of operating members meant for performing various operations. Moreover, in the operating unit 22, an instrument channel port 223 is formed which is communicated with an instrument channel and through which a treatment tool is inserted in the instrument channel.

The universal cord 23 extends from the operating unit 22, and represents a cable in which a plurality of signal cables is laid for transmitting various signals and an optical fiber is laid for transmitting the illumination light supplied from the light source device 6.

The connector 24 is installed at the front end of the universal cord 23. The connector 24 includes a first connector unit 241 to a third connector unit 243 to which an ultrasound cable 31, a video cable 41, and the light source device 6 are respectively connected.

The ultrasound imaging apparatus 3 is electrically connected to the ultrasound endoscope 2 via the ultrasound cable 31 (see FIG. 1); sends electrical pulse signals to the ultrasound endoscope 2 via the ultrasound cable 31; irradiates the ultrasound endoscope 2 with ultrasound waves; receives electrical echo signals obtained as a result of conversion of the ultrasound echo received by the ultrasound endoscope 2; and generates ultrasound images.

The endoscope imaging apparatus 4 is electrically connected to the ultrasound endoscope 2 via the video cable 41 (see FIG. 1) and receives input of image signals from the ultrasound endoscope 2 via the video cable 41. Then, the endoscope imaging apparatus 4 performs predetermined processing with respect to the image signals and generates endoscope images.

The display device 5 is configured using liquid crystals or organic EL (Electro Luminescence), or using a projector, or using a CRT (Cathode Ray Tube); and displays the ultrasound images generated by the ultrasound imaging apparatus 3 and displays the endoscope images generated by the endoscope imaging apparatus 4.

The light source device 6 is connected to the ultrasound endoscope 2, and provides an illumination light to the ultrasound endoscope 2 for illuminating the inside of the subject.

Figure 2:
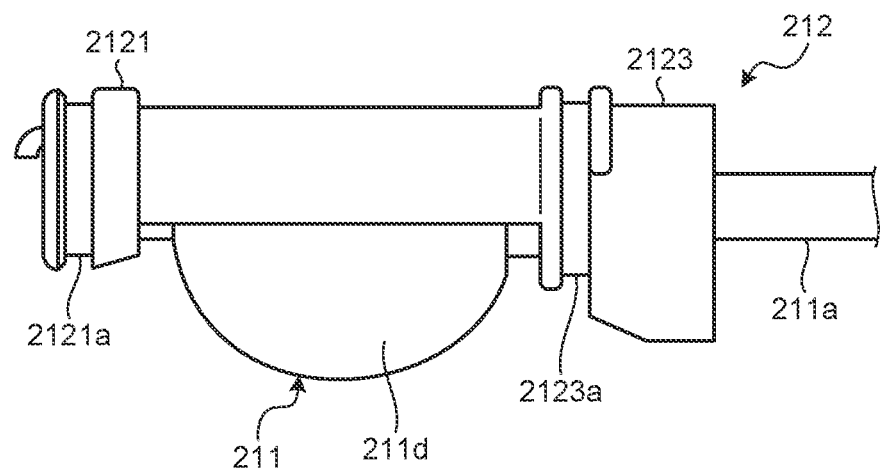
FIG. 2 is a diagram illustrating a lateral view of the front end of the ultrasound endoscope.

Given below is the explanation of a detailed configuration of the insertion portion 21. FIG. 2 is a diagram illustrating a lateral view of the front end of the ultrasound endoscope. As illustrated in FIG. 2, the ultrasound endoscope 2 includes a first rigid portion 2121 that is positioned at the front end of the insertion portion 21 which gets inserted inside the subject; a supporting portion 2122 that is connected to the proximal end of the first rigid portion 2121; and a second rigid portion 2123 that is connected to the proximal end of the supporting portion 2122.

In the first rigid portion 2121 and the second rigid portion 2123, a first band groove 2121a and a second band groove 2123a are respectively formed to lock balloon bands provided in a balloon, so that the balloon gets attached to the ultrasound endoscope 2.

Figure 3:
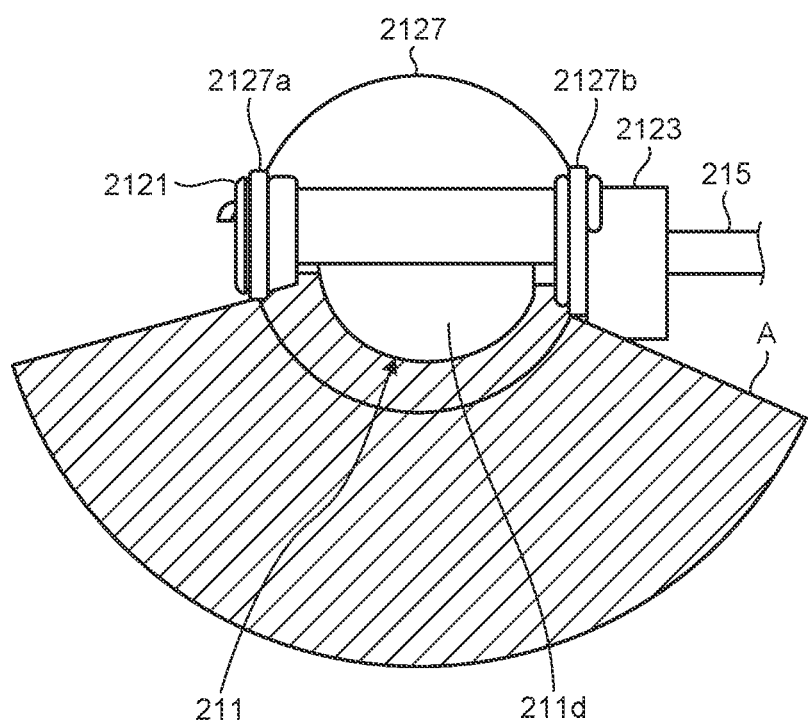
FIG. 3 is a diagram illustrating the state attained by attaching a balloon to the state illustrated in FIG. 2.

FIG. 3 is a diagram illustrating the state attained by attaching a balloon to the state illustrated in FIG. 2. As illustrated in FIG. 3, of a tubular balloon 2127, a balloon band 2127a at the front end is fit in the first band groove 2121a, and a balloon band 2127b at the proximal end is fit in the second band groove 2123a; and hence the balloon 2127 gets attached to the front end of the insertion portion 21 and covers the ultrasound transducer 211. In the state in which the balloon 2127 is attached to the insertion portion 21, when a liquid such as water is filled in the balloon 2127 from balloon water supply/water drainage conduits 2123d, the balloon 2127 expands. When the ultrasound transducer 211 is driven under the control of the ultrasound imaging apparatus 3; as illustrated in FIG. 3, an ultrasound image can be generated in a region A having the cross-sectional surface along the direction of arrangement of a plurality of piezoelectric elements.

Figure 4:
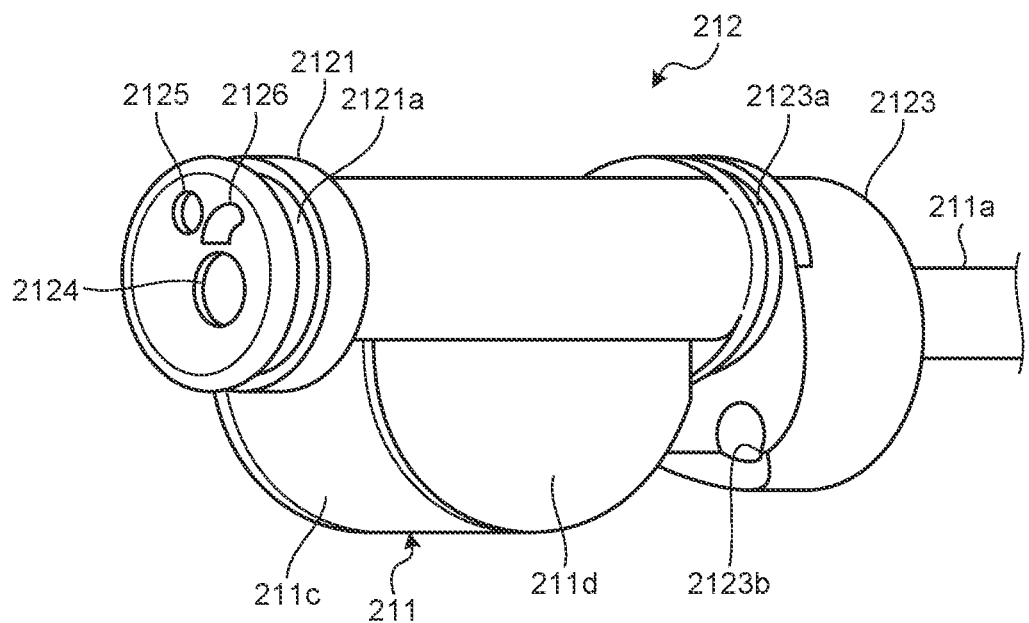
FIG. 4 is a perspective view of the front end of the ultrasound endoscope illustrated in FIG. 1, when viewed from the front end side.
Figure 5:
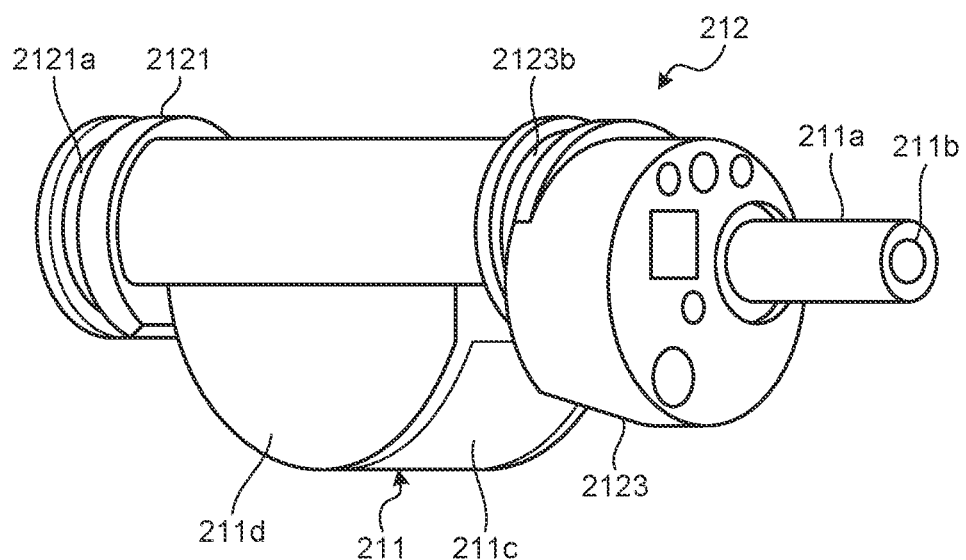
FIG. 5 is a perspective view of the front end of the ultrasound endoscope illustrated in FIG. 1, when viewed from the proximal end side.
Figure 6:
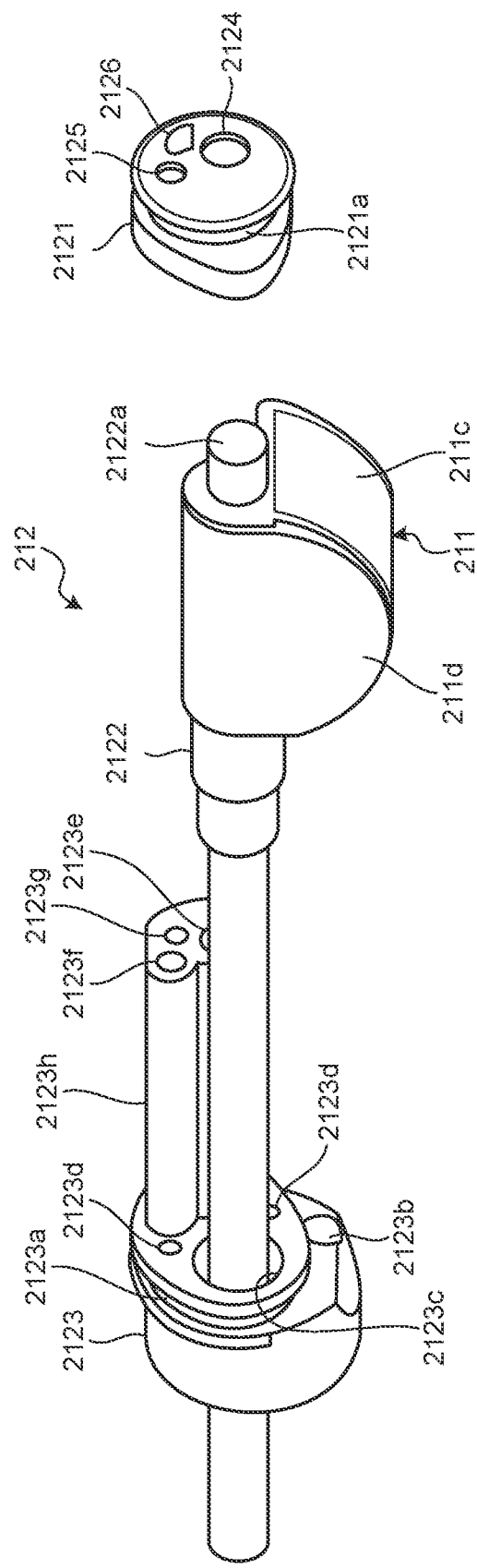
FIG. 6 is an exploded view of FIG. 4.
Figure 7:
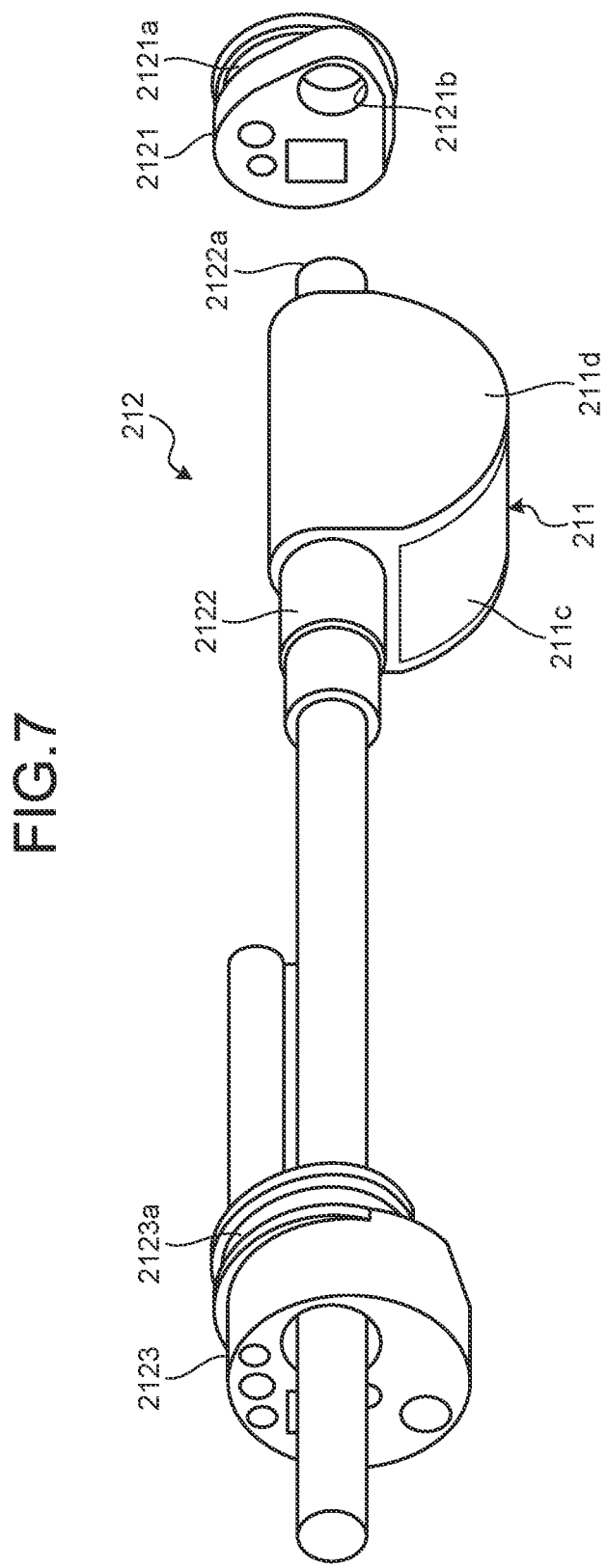
FIG. 7 is an exploded view of FIG. 5.

FIG. 4 is a perspective view of the front end of the ultrasound endoscope illustrated in FIG. 1, when viewed from the front end side. FIG. 5 is a perspective view of the front end of the ultrasound endoscope illustrated in FIG. 1, when viewed from the proximal end side. FIG. 6 is an exploded view of FIG. 4. FIG. 7 is an exploded view of FIG. 5.

At the front end of the first rigid portion 2121, the following units are installed: an imager 2124 that captures images along the longitudinal direction of the insertion portion 21; an illuminating unit 2125 that illuminates the inside of the subject with the illumination light supplied from the light source device 6; and a nozzle 2126 that is used to spray a liquid such as water from the front end of the insertion portion 21 toward the imager 2124 with the aim of removing dirt attached to the imager 2124.

As illustrated in FIG. 5, the ultrasound transducer 211 has the flexible shaft 211a connected thereto for transmitting the power of a rotation mechanism. In the flexible shaft 211a is inserted a plurality of signal lines 211b that is electrically connected to the piezoelectric elements of the ultrasound transducer 211. The flexible shaft 211a is, for example, a coil-shaped metallic member that rotates due to the power of the rotation mechanism and causes rotation of the ultrasound transducer 211 that is fixed to the front end of the flexible shaft 211a. At that time, the flexible shaft 211a and a plurality of signal lines 211b rotate in an integrated manner. As a result of inserting the signal lines through the inside of the flexible shaft 211a, the internal space of the flexible shaft 211a can be effectively utilized, thereby making it possible to make the insertion portion 21 thinner. Meanwhile, the signal lines 211b need not always be inserted through the flexible shaft 211a, and can alternatively be placed on the outside of the flexible shaft 211a. That eliminates the need to perform the task of inserting a plurality of signal lines 211b through the elongated flexible shaft 211a. Meanwhile, a rotation supporting member such as a shaft bearing can be disposed in between the flexible shift 211a and the second rigid portion 2123, so that the flexible shaft 211a can smoothly rotate with respect to the second rigid portion 2123.

The first rigid portion 2121 is made of, for example, resin. However, there is no particular restriction on the material of the first rigid portion 2121. Thus, the first rigid portion 2121 can be made of a metal or an alloy. In the ultrasound endoscope 2, in the state in which the ultrasound transducer 211 is covered by the balloon 2127 and a liquid such as degassed water is filled in the balloon 2127, the balloon 2127 is brought into contact with the body tissue, so that the ultrasound waves are transmitted more easily from the ultrasound transducer 211 toward the body tissue. At the proximal end of the first rigid portion 2121, a depressed portion 2121b (see FIG. 7) is formed in which the front end of the supporting portion 2122 fits. In between the supporting portion 2122 and the depressed portion 2121b, a rotation supporting member such as a shaft bearing is disposed so that the ultrasound transducer 211 can rotate smoothly.

The supporting portion 2122 is a rod-like member that has the long side along the longitudinal direction of the insertion portion 21. The supporting portion 2122 is made of, for example, a metal or an alloy; but there is not particular restriction on the material of the supporting portion 2122. To the supporting portion 2122, the flexible shaft 211a is attached in such a way that the supporting portion 2122 rotates accompanying the rotation of the flexible shaft 211a. Moreover, the supporting portion 2122 has the ultrasound transducer 211 fixed thereto. Thus, accompanying the rotation of the flexible shaft 211a, the supporting portion 2122 and the ultrasound transducer 211 can be rotated in an integrated manner. At the front end of the supporting portion 2122, a salient portion 2122a is formed to fit in the depressed portion 2121b of the first rigid portion 2121. Meanwhile, alternatively, a salient portion can be formed on the first rigid portion 2121, and a depressed portion can be formed in the supporting portion 2122.

The second rigid portion 2123 is made of, for example, resin. However, there is no particular restriction on the material of the second rigid portion 2123. Moreover, in the second rigid portion 2123, an instrument channel outlet 2123b is formed through which the treatment tool inserted from a side of the proximal end is made to protrude along the longitudinal direction of the insertion portion 21. The instrument channel outlet 2123b is formed to be communicated with an instrument channel. Moreover, in the instrument channel outlet 2123b, a forceps standup mechanism (not illustrated) can be disposed so that the orientation of the treatment tool, which is protruding from the instrument channel outlet 2123b, can be guided in the direction in which the ultrasound transducer 211 radiates the ultrasound waves. Furthermore, in the second rigid portion 2123, an oscillator conduit 2123c is disposed in which the proximal end of the supporting portion 2122 is inserted. In between the supporting portion 2122 and the oscillator conduit 2123c, a rotation supporting member such as a shaft bearing can be disposed so as to ensure smooth rotation.

Figure 8:
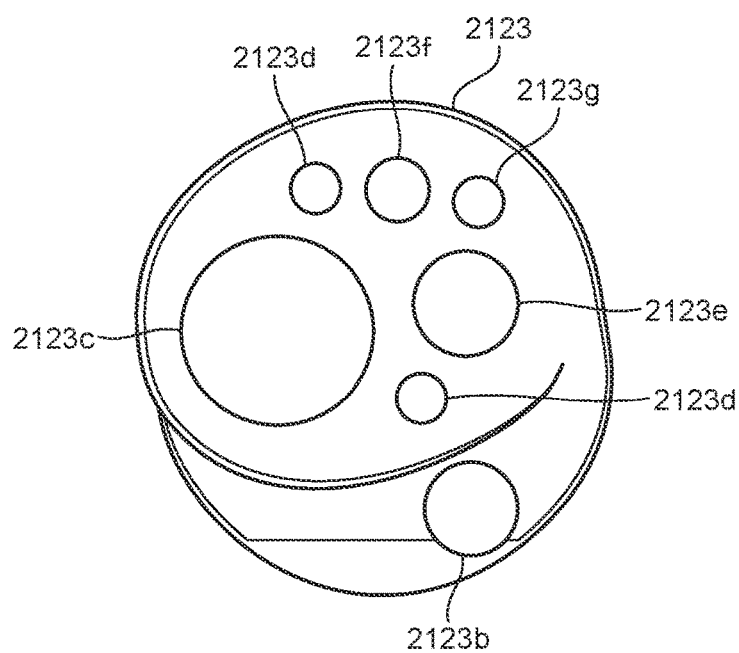
FIG. 8 is a diagram illustrating a second rigid portion when viewed from the front end side.

FIG. 8 is a diagram illustrating the second rigid portion when viewed from the front end side. As illustrated in FIG. 8, the following components are formed in the second rigid portion 2123: the oscillator conduit 2123c through which the flexible shaft 211a and the signal lines 211b are inserted; the balloon water supply/water drainage conduits 2123d that are used for supplying a liquid into the balloon attached to cover the ultrasound transducer 211 and for draining the liquid from the inside of the balloon; an imaging signal line conduit 2123e through which signal lines for imaging that are connected to the imaging element of the imager 2124 are inserted; a light guide conduit 2123f through which the light guide that is used to transmit light to the illumination lens of the illuminating unit 2125 is inserted; and a water supply conduit 2123g that is used to supply a liquid to the nozzle 2126. Meanwhile, the two balloon water supply/water drainage conduits 2123d illustrated in FIG. 8 include a conduit for supplying a liquid into the balloon and a conduit for draining the liquid from the inside of the balloon. However, alternatively, only a single conduit can be configured to supply the water as well as drain the water.

Moreover, as illustrated in FIG. 6, the second rigid portion 2123 includes a columnar portion 2123h that extends up to the first rigid portion 2121. Inside the columnar portion 2123*h* are formed the imaging signal line conduit 2123*e*, the light guide conduit 2123*f*, and the water supply conduit 2123*g*. The front end of the columnar portion 2123*h* is fixed to the first rigid portion 2121. Hence, even when the flexible shaft 211*a* and the supporting portion 2122 rotate, the first rigid portion 2121 and the second rigid portion 2123 do not rotate. Meanwhile, either the columnar portion 2123*h* can be formed in an integrated manner with the second rigid portion 2123, or the columnar portion 2123*h* formed as a separate portion from the second rigid portion 2123 can be fixed to the second rigid portion 2123.

The openings of the balloon water supply/water drainage conduits 2123*d* can for formed at any positions in between the first band groove 2121*a* and the second band groove 2123*a*. At the front end of the columnar portion 2123*h*, the openings of the imaging signal line conduit 2123*e*, the light guide conduit 2123*f*, and the water supply conduit 2123*g* are formed. The columnar portion 2123*h* and the first rigid portion 2121 are paired in such a way that the positions of those openings are coincident with the imager 2124, the illuminating unit 2125, and the nozzle 2126 in the first rigid portion 2121, respectively.

Meanwhile, it is desirable that the flexible shaft 211*a*, which extends from the second rigid portion 2123 to the proximal end of the insertion portion 21, is placed to pass through the inside of a tube. That is desirable for the reason that, since the insertion portion 21 has a light guide placed therein, the rotating flexible shaft 211*a* is to be prevented from interfering with the light guide and damaging it.

Figure 9:
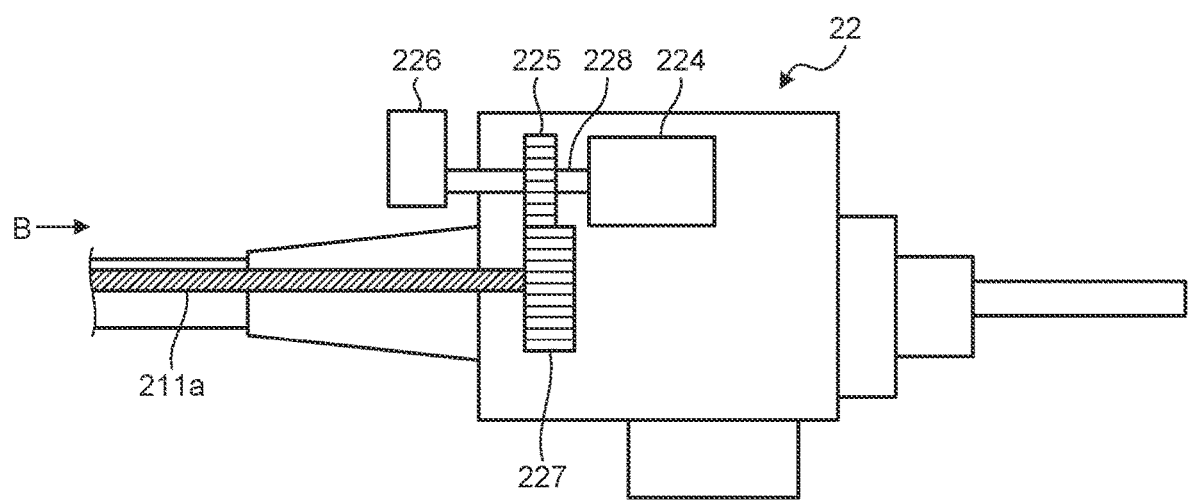
FIG. 9 is a schematic configuration diagram of a connector.

FIG. 9 is a schematic configuration diagram of the connector. Inside the connector 24, a motor 224 is installed for rotating the ultrasound transducer 211. As the motor 224, it is possible to use a stepping motor that can be rotated at an arbitrary angle according to the drive pulse current, or to use a servo motor that is combined with a detection device meant for detecting the rotation angle and the rotation count. The motor 224 has a shaft 228 installed therein, and the shaft 228 has a first gear 225 attached thereto. Moreover, at the end of the flexible shaft 211*a*, a second gear 227 is attached. The first gear 225 and the second gear 227 are configured to mesh with each other and rotate in tandem. Thus, when the motor 224 is rotated, the power can be transmitted to the flexible shaft 211*a* via the shaft 228, the first gear 225, and the second gear 227. In the present working example, the configuration includes two gears for transmitting the power. However, that is not the only possible case, and the number of gears can be increased or reduced as may be necessary. Besides, as long as the power of the motor 224 can be transmitted to the flexible shaft 211*a*, it is not required to use a gear and alternatively, for example, a dynamic belt can be used. As explained above, inside the connector 24, a rotation mechanism is housed that includes the motor 224 meant for rotating the ultrasound transducer 211 and includes a transmission mechanism configured with the first gear 225 and the second gear 227. Moreover, the shaft 228 has a lever 226 attached thereto. When the lever 226 is manually rotated, the shaft 228 rotates and, in tandem with the rotation of the shaft 228, the ultrasound transducer 211 can be rotated via the flexible shaft 211*a*.

Figure 10:
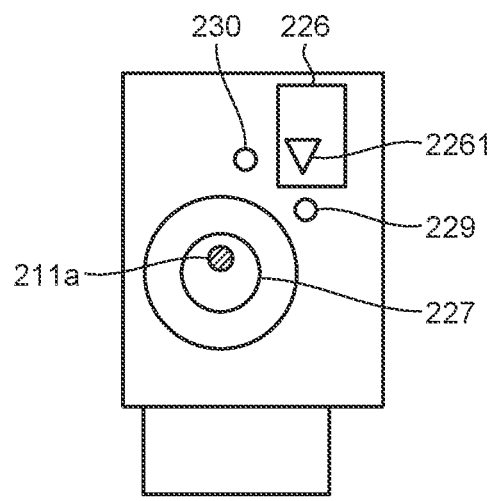
FIG. 10 is a view taken along an arrow B illustrated in FIG. 9.

FIG. 10 is a view taken along an arrow B illustrated in FIG. 9. As illustrated in FIG. 10, the lever 226 includes an indicator 2261 as an angle display portion for displaying the angle of the ultrasound transducer 211 in the direction of its rotation. For example, when the indicator 2261 is oriented in the direction of a first mark 229, it is indicated that the orientation of the ultrasound transducer 211 is such that the insertion portion 21 is easily insertable into the body of the subject. On the other hand, when the indicator 2261 is oriented in the direction of a second mark 230, it is indicated that the orientation of the ultrasound transducer 211 is such that, even when a treatment tool is made to protrude from the instrument channel outlet 2123*b*, the treatment tool and the ultrasound transducer 211 do not come in contact with each other.

Figure 11:
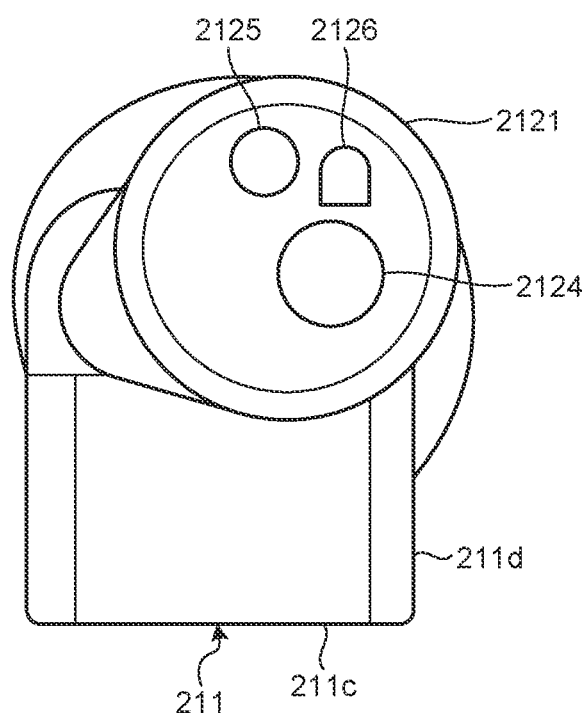
FIGS. 11 and 12 are front views of the front end of the ultrasound endoscope.
Figure 12:
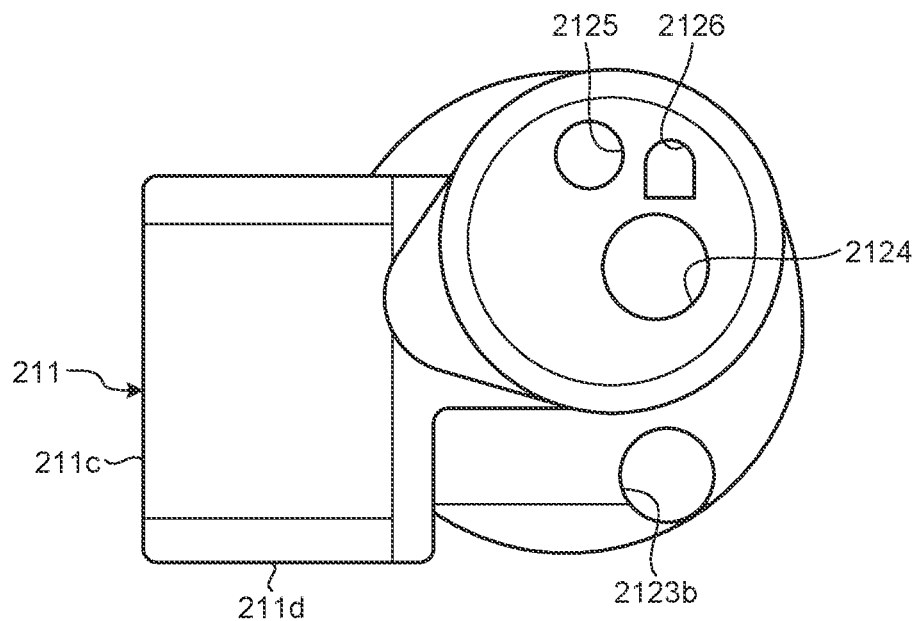

FIGS. 11 and 12 are front views of the front end of the ultrasound endoscope. When at the angle illustrated in FIG. 11, the ultrasound transducer 211 overlaps, in the longitudinal direction of the insertion portion 21, with the portion that is bulging due to the instrument channel outlet 2123*b* of the second rigid portion 2123. Hence, a projection area that is obtained by projecting the insertion portion 21 in the longitudinal direction of the insertion portion 21 is the smallest. In other words, the acoustic lens of the ultrasound transducer 211 gets oriented in the direction in which the distance from the center of the oscillator conduit 2123*c* of the second rigid portion 2123 to the outer periphery of the second rigid portion 2123 is the longest. Thus, by adjusting the angle of the ultrasound transducer 211, it can be oriented in such a way that the cross-sectional area of the front end portion 212, which has the orthogonal orientation to the longitudinal direction of the insertion portion 21, is the smallest. As a result, the insertion portion 21 can be made easily insertable into the body of the subject and easily removable from the body of the subject.

On the other hand, when the ultrasound transducer 211 is at the angle illustrated in FIG. 12, the treatment tool protruding from the instrument channel outlet 2123*b* does not make contact with the ultrasound transducer 211.

Given below is the explanation of an observation method implemented using the ultrasound endoscope 2. Firstly, the ultrasound endoscope 2 is operated and, in the state in which the insertion portion 21 having the balloon 2127 attached thereto is inserted into the body of the subject, the ultrasound transducer 211 is placed in the vicinity of the site of lesion by referring to an optical observation image taken using the imaging optical system. Then, while maintaining that state, degassed water is sent into the balloon 2127 using the balloon water supply/water drainage conduits 2123*d*, so that the balloon 2127 expands. Subsequently, in the state in which the expanded balloon 2127 is pressed against the body wall of the subject, the ultrasound imaging apparatus 3 is operated and electrical signals are sent to the ultrasound transducer 211, so that ultrasound waves are generated by the ultrasound transducer 211. Moreover, the ultrasound imaging apparatus 3 is operated so as to supply the power for driving the motor 224. As a result of driving the motor 224, the ultrasound transducer 211 rotates via the flexible shaft 211*a*.

Figure 13:
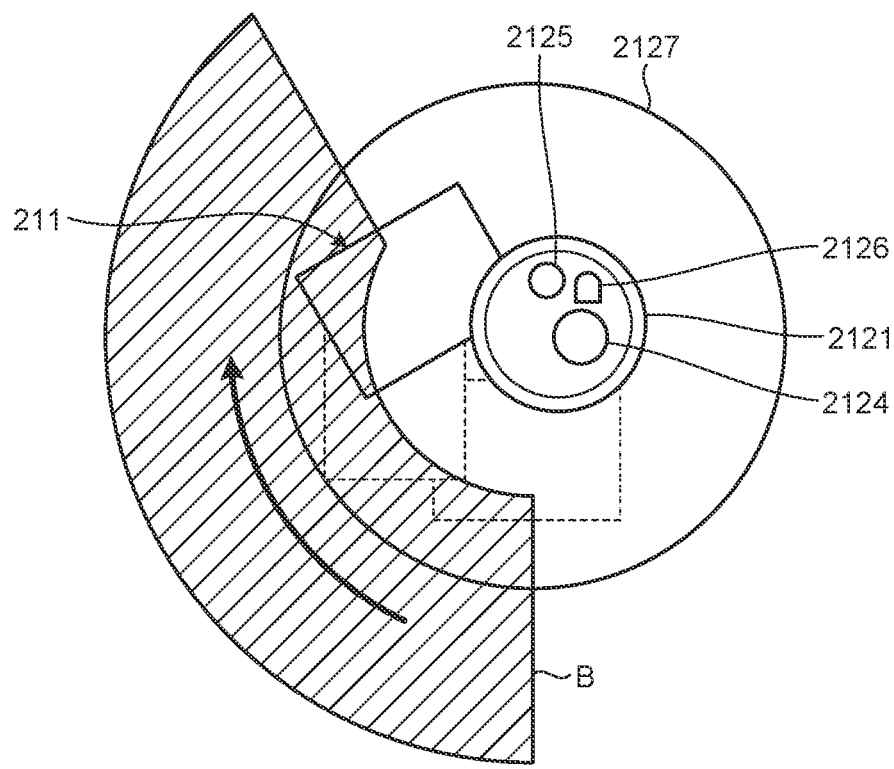
FIG. 13 is a diagram illustrating the rotation of the ultrasound transducer.

FIG. 13 is a diagram illustrating the rotation of the ultrasound transducer. As illustrated in FIG. 13, the ultrasound transducer 211 rotates by a predetermined angle R from the position illustrated in FIG. 11. In other words, the ultrasound transducer 211 oscillates at a certain angle R. Herein, the angle R can be set in the range from 30° to 180°. With such a configuration, in addition to electronically scanning the ultrasound transducer 211 in the direction of arrangement of the piezoelectric elements, the ultrasound transducer 211 is mechanically scanned around the axis of the supporting portion 2122. Regarding the mechanical scanning, by establishing association with the information about a detection device that detects the pulse current and the rotation angle at the time of driving the motor 224, three-dimensional echo information included in the angle R can be obtained as illustrated in FIG. 13. The ultrasound imaging apparatus 3 in which such information is sequentially obtained and stored becomes able to generate a three-dimensional image based on that information.

Meanwhile, the ultrasound endoscope 2 is not limited to the embodiment described above. Alternatively, a rotation mechanism such as a motor can be installed in the operating unit 22. In that case, the flexible shaft 211a is no more required to be placed up to the inside of the universal code 23, and hence can be shortened in length. As a result of shortening the length of the flexible shaft 211a, the distance between the motor 224 and the ultrasound transducer 211 can be reduced. That enables achieving enhancement in the transmissibility of the torque.

Moreover, the motor 224 can be disposed in the connector 24, and a detection device for detecting the rotation angle can be disposed in the operating unit 22 or the front end portion 212. In this way, by placing the detection device close to the ultrasound transducer 211, the rotation angle of the ultrasound transducer 211 can be detected with more accuracy.

As another working example, a rotation mechanism such as a motor can be disposed in the front end portion 212. In that case, the configuration need not include the flexible shaft 211a. As a result, a more preferable rotation action can be achieved without any effect of the flexure of the flexible shaft 211a.

The ultrasound imaging apparatus 3 can have the function of displaying the angle, which is detected by an angle sensor, in the display device 5. Moreover, the ultrasound imaging apparatus 3 can have the function of displaying, in the display device 5, the angle of the ultrasound transducer 211 at which the projection area obtained by projecting the insertion portion 21 in the longitudinal direction of the insertion portion 21 is the smallest. Furthermore, the ultrasound imaging apparatus 3 can have the function of displaying, in the display device 5, the angle of the ultrasound transducer 211 at which there is no contact between the treatment tool, which is protruding from the instrument channel outlet 2123b, and the ultrasound transducer 211.

The operator becomes able to observe two-dimension ultrasound images as well as to observe three-dimensional ultrasound images at arbitrary timings. Regarding the two-dimensional ultrasound images obtained in a conventional ultrasound endoscope, the observation area is narrow and there are not many clues enabling identification of the observed body part. On the other hand, in the ultrasound endoscope 2 according to the disclosure, there is a wide observable range, and the ultrasound images can be confirmed in the three-dimensional display too. Hence, it becomes easier to understand the site of lesion.

Modification Example

The ultrasound endoscope according to a modification example includes an imager that is installed in the second rigid portion and that takes images in the direction intersecting with the longitudinal direction of the insertion portion. Thus, the ultrasound endoscope is not limited to the direct viewing type as explained in the embodiment, and can alternatively be an oblique-viewing endoscope in which the imager is positioned at the proximal end of the ultrasound transducer.

Moreover, in the first rigid portion of the ultrasound endoscope, an instrument channel outlet is formed for enabling protrusion of a treatment tool, which is inserted from the proximal end, along the longitudinal direction of the insertion portion. Thus, in the ultrasound endoscope, although a treatment tool can be made to protrude from the proximal end of the ultrasound transducer as explained in the embodiment, it can alternatively be made to protrude from the front end of the ultrasound transducer. Furthermore, in the ultrasound endoscope, although a treatment tool can be made to protrude along the longitudinal direction of the insertion portion 21, it can alternatively be made to protrude in the direction intersecting with the longitudinal direction of the insertion portion 21.

Meanwhile, in the embodiment described above, the first rigid portion 2121 is made of resin. Hence, in case the ultrasound transducer 211 is damaged, it can be removed by breaking the first rigid portion 2121, and can be repaired or replaced.

According to the disclosure, it becomes possible to implement an ultrasound endoscope and an ultrasound system that have a wider observable range in ultrasound images.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
an insertion portion comprising;
a casing including a first rigid portion and a second rigid portion, the first and second rigid portions being two separate discrete bodies and spaced apart from each other in a longitudinal axis direction;
a supporting portion being tubular, the supporting portion is inserted within a corresponding hole in the casing, the supporting portion having a distal end and a proximal end, the distal end of the supporting portion connected to the first rigid portion, the proximal end of the supporting portion connected to the second rigid portion;
an imager installed in the first rigid portion, the imager being configured to capture an image in one of a direction along a longitudinal axis direction of the insertion portion;
a plurality of signal lines connected to the imager, the plurality of signal lines being inserted into an interior of the supporting portion; and
an ultrasound transducer fixed to the supporting portion, the ultrasound transducer including a plurality of piezoelectric elements arranged along a longitudinal axis of the insertion portion, the ultrasound transducer being disposed between the first rigid portion and the second rigid portion; and
an actuator configured to rotate the supporting portion and the ultrasound transducer around the longitudinal axis relative to at least the second rigid portion.

2. The ultrasound endoscope according to claim 1, wherein, the second rigid portion has an instrument channel outlet through which a treatment tool inserted from a proximal end side is made to protrude along a longitudinal axis direction of the insertion portion.

3. The ultrasound endoscope according to claim 1, wherein, the first rigid portion and the second rigid portion each have a balloon groove to lock a respective balloon band.

4. The ultrasound endoscope according to claim 1, further comprising a flexible shaft disposed in the insertion section, the flexible shaft is connected to the ultrasound transducer;

wherein a plurality of signal lines connected to the plurality of piezoelectric elements of the ultrasound transducer is inserted through the flexible shaft.

5. The ultrasound endoscope according to claim 1, wherein the ultrasound transducer is a convex ultrasound transducer in which a longitudinal direction of the plurality of piezoelectric elements is orthogonal to the longitudinal axis of the insertion portion and the plurality of piezoelectric elements are arranged to form a curved surface.

6. The ultrasound endoscope according to claim 1, wherein the first rigid portion is made of resin.

7. The ultrasound endoscope according to claim 1, further comprising an angle sensor configured to detect an angle in a direction of rotation of the ultrasound transducer.

8. The ultrasound endoscope according to claim 7, further comprising an angle display configured to display the angle in the direction of rotation of the ultrasound transducer as detected by the angle sensor.

9. The ultrasound endoscope according to claim 1, further comprising:
a rotatable marker rotatable with the ultrasound transducer;
a fixed marker fixed relative to the rotatable marker, the fixed marker being configured to indicate, when the rotatable marker is aligned with the fixed marker, that a rotation amount of the ultrasound transducer is in a state in which a projection area that is obtained by projecting the insertion portion in the longitudinal direction of the insertion portion is smallest.

10. The ultrasound endoscope according to claim 2, further comprising:
a rotatable marker rotatable with the ultrasound transducer;
a fixed marker fixed relative to the rotatable marker, the fixed marker being configured to indicate, when the rotatable marker is aligned with the fixed marker, that a rotation amount of the ultrasound transducer is in a state in which the treatment tool protruding from the instrument channel outlet is not in contact with the ultrasound transducer.

11. An endoscope system comprising: an ultrasound endoscope; an ultrasound imaging apparatus configured to generate an ultrasound image;
and an image display configured to display the ultrasound image generated by the ultrasound imaging apparatus;
the ultrasound endoscope comprising:
an insertion portion, the insertion portion comprising:
a casing including a first rigid portion and a second rigid portion, the first and second rigid portions being two separate discrete bodies and spaced apart from each other in a longitudinal axis direction;
a supporting portion being tubular, the supporting portion is inserted within a corresponding hole in the casing, the supporting portion having a distal end and a proximal end,
the distal end of the supporting portion connected to the first rigid portion,
the proximal end of the supporting portion connected to the second rigid portion,
an imager installed in the first rigid portion, the imager being configured to capture an image in one of a direction along a longitudinal axis direction of the insertion portion;
a plurality of signal lines connected to the imager, the plurality of signal lines being inserted into an interior of the supporting portion; and
and an ultrasound transducer fixed to the supporting portion, the ultrasound transducer including a plurality of piezoelectric elements arranged along a longitudinal axis of the insertion portion, the ultrasound transducer being disposed between the first rigid portion and the second rigid portion;
and an actuator configured to rotate the supporting portion and the ultrasound transducer, wherein the ultrasound imaging apparatus is configured to determine whether the ultrasound transducer is in a first state in which a projection area that is obtained by projecting the insertion portion in the longitudinal direction of the insertion portion is smallest;
and the image display displays a first indication of whether the ultrasound transducer is in the first state.

12. The endoscope system according to claim 11, further comprising an angle sensor configured to detect a rotation amount in a direction of rotation of the ultrasound transducer and the first indication of whether the ultrasound transducer is in the first state comprises the rotation amount detected by the angle sensor.

13. The endoscope system according to claim 12, wherein the ultrasound imaging apparatus is further configured to generate a three-dimensional image by synthesizing the ultrasound image according to the rotation amount detected by the angle sensor.

14. The endoscope system according to claim 11, wherein
the second rigid portion has an instrument channel outlet through which a treatment tool inserted from a proximal end side is made to protrude along the longitudinal direction of the insertion portion, and
the ultrasound imaging apparatus is configured to determine whether the ultrasound transducer is in a second state in which the treatment tool protruding from the instrument channel outlet is not in contact with the ultrasound transducer,
the image display displays a second indication of whether the ultrasound transducer is in the second state.

15. The ultrasound endoscope according to claim 1, wherein the actuator is configured to rotate the supporting portion and the ultrasound transducer around the longitudinal axis relative to the first rigid portion and relative to the second rigid portion.

16. The ultrasound endoscope according to claim 1, further comprising an illumination lens installed in the first rigid portion and a light guide configured to transmit light to the illumination lens, the light guide is inserted into the supporting portion.

17. The ultrasound endoscope according to claim 16, further comprises a nozzle installed in the first rigid portion and a liquid supply conduit configured to supply a liquid to the nozzle, the liquid supply conduit is inserted into the supporting portion.

18. The endoscope system according to claim 11, wherein the second rigid portion further comprising an instrument channel outlet through which a treatment tool inserted from a proximal end side is made to protrude along the longitudinal direction of the insertion portion; and
the ultrasound endoscope comprising:
a rotatable marker rotatable with the ultrasound transducer; and
one or more of:
a first fixed marker fixed relative to the rotatable marker, the first fixed marker being configured to indicate, when the rotatable marker is aligned with the first fixed marker, that the rotation amount of the ultrasound transducer is in a first state in which a projection area that is obtained by projecting the insertion portion in the longitudinal direction of the insertion portion is smallest; and a second fixed marker fixed relative to the rotatable marker, the second fixed marker being configured to indicate, when the rotatable marker is aligned with the second fixed marker, that a rotation amount of the ultrasound transducer is in a second state in which the treatment tool protruding from the instrument channel outlet is not in contact with the ultrasound transducer.

19. The ultrasound endoscope according to claim 1, wherein the ultrasound transducer protrudes radially outside of a longitudinal projection of at least the second rigid end portion of the casing.

* * * * *